United States Patent
Kohli

(10) Patent No.: US 7,356,478 B1
(45) Date of Patent: Apr. 8, 2008

(54) SECURE MEDICAL FACILITY REPORT PREPARATION AND DELIVERY

(75) Inventor: James F. Kohli, Waukesha, WI (US)

(73) Assignee: GE Medical Systems, Inc., Pewaukee, WI (US)

( * ) Notice: Subject to any disclaimer, the term of this patent is extended or adjusted under 35 U.S.C. 154(b) by 1447 days.

(21) Appl. No.: 09/619,957

(22) Filed: Jul. 20, 2000

(51) Int. Cl.
G06Q 10/00 (2006.01)

(52) U.S. Cl. ............... 705/2; 705/3; 702/185

(58) Field of Classification Search .......... 705/2, 705/3; 702/185; 345/807; 707/104.1
See application file for complete search history.

(56) References Cited

U.S. PATENT DOCUMENTS

| | | | | |
|---|---|---|---|---|
| 4,899,292 A | * | 2/1990 | Montagna et al. ....... | 707/104.1 |
| 5,655,084 A | * | 8/1997 | Pinsky et al. ................. | 705/3 |
| 5,995,939 A | * | 11/1999 | Berman et al. ................ | 705/3 |
| 6,006,191 A | * | 12/1999 | DiRienzo ..................... | 705/2 |
| 6,260,021 B1 | * | 7/2001 | Wong et al. .................. | 705/2 |
| 6,272,469 B1 | * | 8/2001 | Koritzinsky et al. ......... | 705/2 |
| 6,598,011 B1 | * | 7/2003 | Howards Koritzinsky et al. ......................... | 702/185 |
| 6,603,494 B1 | * | 8/2003 | Banks et al. ................. | 345/807 |

OTHER PUBLICATIONS

James DeOrio, Surgical templates for orthopedic operative reports, Jun. 2002, Orthopedics, vol. 25, Iss. 6. p. 639, 4 pgs.*

* cited by examiner

Primary Examiner—Robert W Morgan
(74) Attorney, Agent, or Firm—Fletcher Yoder

(57) ABSTRACT

A technique is provided for securely generating reports for biomedical equipment in a medical institution. Equipment data is collected, manually or automatically. The data is stored in a centralized database operating in a secure processing space, such as at a service provider location. The database is accessed periodically, or upon request, to generate data files for report generation. The data accessed may be used to derive or calculate other data for the reports, such at trending data, equipment counts, comparisons, and so forth. The data file is then exported through a firewall to a second processing space. The report is compiled in the second processing space, and is formatted in accordance with a report template, such as for transmission to the medical institution. An additional firewall separates the second processing space from intrusion, but permits the report to be accessed by the institution via a network such as the Internet.

36 Claims, 20 Drawing Sheets

FIG. 13

FAILURE CATEGORY BENCHMARK SUMMARY TABLE (ALL FAILURES)

| FAILURE CATEGORY STATUS | STATUS | FAILURES UNDER CONTRACT | REFERENCE RANGE | REASON FOR NO STATUS |
|---|---|---|---|---|
| OTHER | ☐ | 903 | .0001 TO .0005 | |
| COMPUTER | ☐ | 144 | -.0003 TO .0004 | |
| ELECTRICAL | ☐ | 779 | .0003 TO .0011 | |
| UNKNOWN | ☐ | 9 | -.0002 TO .0002 | |
| MECHANICAL | ☐ | 1305 | .0002 TO .0009 | |
| OPERATOR | ☐ | 160 | -.0003 TO .0004 | |

☐ WITHIN REFERENCE RANGE  ☐ OUTLIERS
☐ OUTSIDE REFERENCE RANGE  ☐ INSUFFICIENT DATA

FIG. 17

EQUIPMENT COUNT BENCHMARK

| EQUIPMENT BY SUB-MODALITY | STATUS | ACTUAL COUNT | REFERENCE RANGE | REASON FOR NO STATUS |
|---|---|---|---|---|
| SUB 1 | ☐ | 34 | 6 TO 21 | REASON 1 |
| SUB 2 | ☐ | 1 | 28 TO 80 | REASON 2 |
| . | ☐ | 5 | 25 TO 131 | . |
| . | ☐ | 7 | 8 TO 23 | . |
| . | ☐ | 25 | 4 TO 22 | . |
|  | ☐ | 26 | 12 TO 24 |  |
|  | ☐ | 8 | 2 TO 7 |  |
|  | ☐ | 11 | 9 TO 42 |  |
|  | ☐ | 265 | 114 TO 272 |  |
|  | ☐ | 90 | 22 TO 97 |  |
|  | ☐ | 57 | 13 TO 63 |  |
|  | ☐ | 19 | 3 TO 21 |  |
|  | ☐ | 148 | 63 TO 165 |  |
|  | ☐ | 2 | 1 TO 4 |  |
|  | ☐ | 383 | 230 TO 915 |  |
|  | ☐ | 2 | 0 TO 6 |  |

REPORTS CONTINUES ON NEXT PAGE

☐ WITHIN REFERENCE RANGE ☐ OUTLIERS
☐ OUTSIDE REFERENCE RANGE ☐ INSUFFICIENT DATA

FIG. 19

SERVICE COVERAGE REPORT
EQUIPMENT WARRANTY BY FULL SERVICE

| DEPARTMENT | LOCATION | GROUP | EQUIP TYPE | MANUFACTURER | MANUAL | MODEL # | ACQ. DATE | CONTROL # | SERIAL # | SERVICE PROVIDER | EXP / RENEWAL DATE |
|---|---|---|---|---|---|---|---|---|---|---|---|
| DEPT 1 | LOCATION 1 | | TYPE 1 | | | # | 3/1/98 | # | # | | |
| DEPT 2 | LOCATION 2 | | TYPE 2 | | | # | 6/1/99 | # | # | | |
| . | . | | . | | | . | N/A | . | . | | |
| . | . | | . | | | . | N/A | . | . | | |
| | | | | | | | N/A | | | | |
| | | | | | | | N/A | | | | |

290 — DEPARTMENT
292 — LOCATION
294 — GROUP
296 — EQUIP TYPE
298 — MANUFACTURER/MANUAL/MODEL #
300 — ACQ. DATE
302 — CONTROL #/SERIAL #
304 — SERVICE PROVIDER
306 — EXP / RENEWAL DATE
288 — (table)

FIG. 21

BREAKDOWN DETAILS BY DEPARTMENT * MEAN TIME TO REPAIR
**\*\*MEAN TIME BETWEEN FAILURES**
DEPARTMENT 1

| MANUFACTURER | EQUIPMENT | # OF BKDWNS | BKDWNS PER YR. | CONTROL # | SERIAL # | AGE/TIME SERVICE | MTTR* (DAYS) | MTBF** (MONTHS) |
|---|---|---|---|---|---|---|---|---|
| | | | | | | | | |
| | | | | | | | | |
| | | | | | | | | |
| | | | | | | | | |
| | | | | | | | | |
| | | | | | | | | |
| | | | | | | | | |

| EQUIPMENT SUB-MODALITY | CURRENT COUNT | 2004 FORECAST NEED | POTENTIAL RETIREMENTS BETWEEN NOW AND 2004 | NET ADDITIONAL NEED |
|---|---|---|---|---|
| SUB 1 | 12 | 13 | 8 | 9 |
| SUB 2 | 1 | 1 | 1 | 1 |
| · | 10 | 11 | 7 | 8 |
| · | 4 | 4 | 4 | 4 |
| · | 2 | 2 | 2 | 2 |
|  | 1 | 1 | 1 | 1 |
|  | 12 | 13 | 9 | 10 |
|  | 12 | 13 | 9 | 10 |

SUGGESTED INVENTORY ENHANCEMENT SUMMARY
(5 YEAR FORECAST)
INSTITUTION 1
SUGGESTED INVENTORY REPLACEMENT SUMMARY
BASED ON INDUSTRY DATA – CONTINUED

REPORTS CONTINUE ON NEXT PAGE...

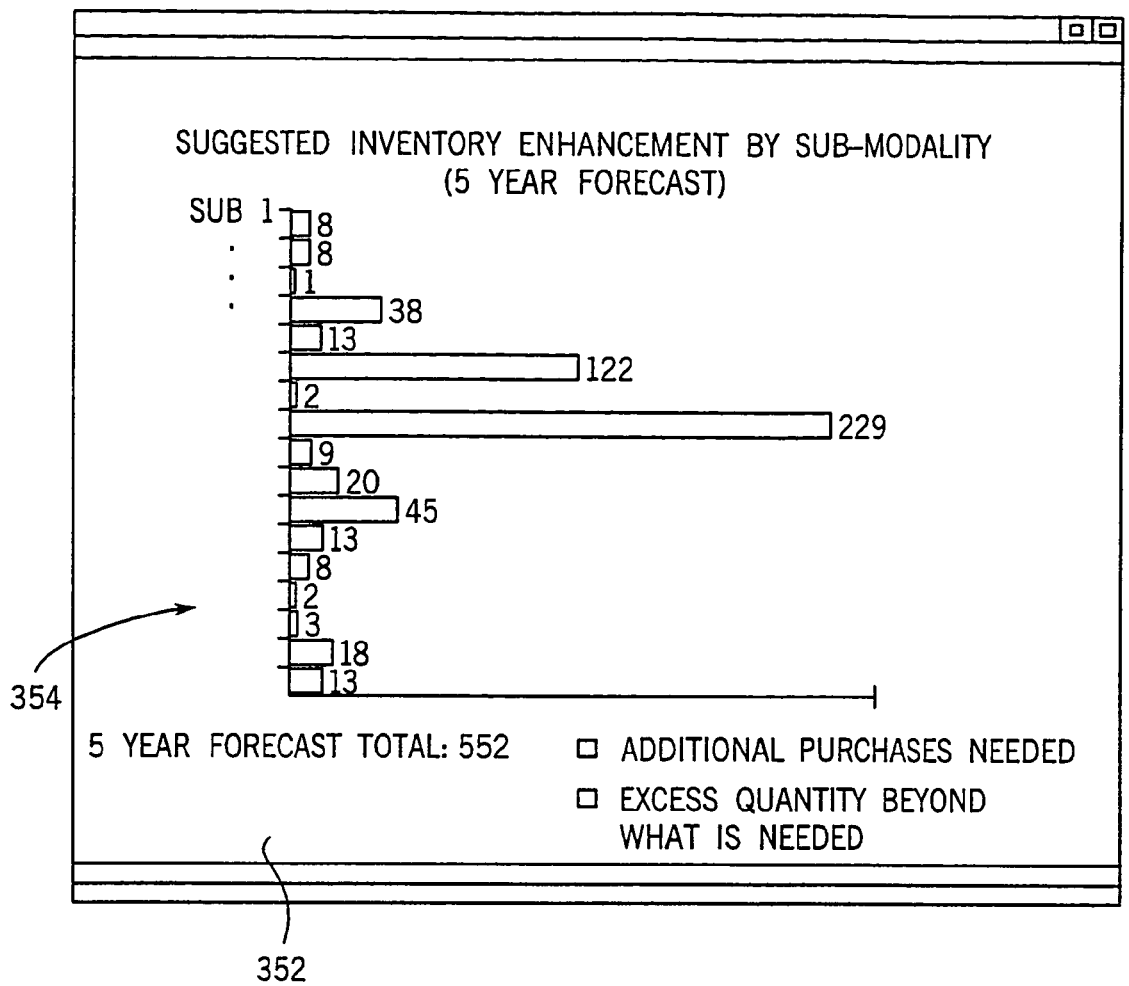

SECURE MEDICAL FACILITY REPORT PREPARATION AND DELIVERY

FIELD OF THE INVENTION

The present invention relates generally to the field of medical diagnostic systems and facilities, and to the management of such facilities. More particularly, the invention relates to a technique for generating and delivering reports regarding activities and operations of medical diagnostic facilities in a secure manner from a central repository of operation data.

BACKGROUND OF THE INVENTION

In the field of medical diagnostics systems and facilities, a wide range of data are collected and utilized for management, diagnostics, and other purposes. In general, modern medical facilities, while providing high quality health care, must function as efficient in viable business. To enable and enhance the efficiencies of such institutions, a variety of techniques have been developed for maintaining both the physical plant, equipment, personnel, and other resources of the institutions. The very nature of medical facilities imposes added constraints and requirements on management techniques. For example, resources of a medical institution must be maintained such that they remain functional and reliable throughout a very demanding schedule. Moreover, the types and quantity of data collected in modern medical diagnostic facilities poses significant demands on data storage, analysis, reporting, and similar management functions.

Several approaches are available and have been adopted by medical diagnostic facilities for management of infrastructure, equipment, personnel, and data. A facility or site may, for example, maintain a staff trained to address a very wide range of equipment, building, and other maintenance concerns. However, for certain types of specialized equipment, such as diagnostics equipment, monitors, imaging equipment, and so forth, many institutions find that outside maintenance or service providers are often cost affective at providing a high level of maintenance and oversight, while freeing the resources of the institution for other matters. In either case, a large amount of information is collected, stored, and managed for analysis and operation of the facility and institution as a business.

Among the data collected and stored for management decisions in medical diagnostic facilities are a range of operational parameters relating to the utilization of the institution's resources. By way of example, data may be collected on information as a diverse as the use of maintenance articles, replacement articles, expendable articles, through to maintenance of highly specialized patient care equipment. Human resources are also commonly managed through detailed schedules, logs, and so forth. Moreover, highly demanding systems are typically provided for analysis of financial and accounting records. Finally, data relating to patient care are collected and stored for use by attending physicians, diagnosing physicians, their staffs, and so forth.

The data collected and stored in a medical diagnostic facility may be placed in any of a range of data repositories. For example, individual departments and systems may include local storage of certain data, while hospital-wide data storage may be provided for some information, such as in a hospital information system (HIS). These systems may also be coupled to other data repositories, such as radiology department informational systems (RIS), picture archiving and communications systems (PACS), and so forth. While certain of the data collected and stored in the institution is less useful for management decisions, much of the data if properly analized may provide key insights useful in capital expenditure decisions, resource allocation decisions, anticipated and past resource utilization reporting, and so forth.

Given the highly sensitive nature of data in medical diagnostic facilities, there is a need, at present, for improved systems designed to access stored data, and to report the stored data, or analyses based upon the stored, for management use. Whether the data repository is a single database or a range of associated databases, and whether the repository is provided on-site or at multiple locations, there is a need in all such systems for a secure technique for accessing the data and for providing reports to users based upon the accessed data.

SUMMARY OF THE INVENTION

The present invention provides a technique for securely accessing and generating reports for medical diagnostic facilities and institutions designed to respond to these needs. The technique may be employed with a wide range of data types, but is particularly well suited to accessing and reporting on management-related information used by the institutions resource-related decisions. The technique may be employed in newly-established information systems, but may also be designed, adapted or retrofitted to existing information systems, such as hospital information systems, radiology department informational systems, and other types of medical facility data management arrangements.

In accordance with certain aspects of the present technique, data is collected and stored in a data repository, which may include one or more databases and physical data storage media. The data repository may be provided at the medical diagnostic facility, but may be conveniently located elsewhere, such as in facilities of a remote service provider contracted by the facility. The data repository operates in a processing space which is secure, having access limited to authorize personnel, such as the service provider. Data for populating reports, particularly management reports are stored in the repository, and are accessed for secure generation of reports. The data file needed for completing the report is created in the secure processing space, and exported to a separate processing space for generation of the report. The report may be assembled by specialized software modules such as a web agent, in the form of user-viewable pages, paper copies, and so forth. In a present embodiment, a web agent is used to populate a report template in the second processing space for distribution users, typically subscribing medical diagnostic facilities and institutions. Distribution may be provided in a range of manners, such as via a wide area network accessed by the subscribing institution, including via the Internet.

BRIEF DESCRIPTION OF THE DRAWINGS

FIGS. 12-25 are exemplary report screens illustrating report analysis for biomedical equipment presenting data for departments, groups, sites, and individual equipment components and types in accordance with aspects of the present technique.

DETAILED DESCRIPTION OF THE INVENTION

Figure 1:
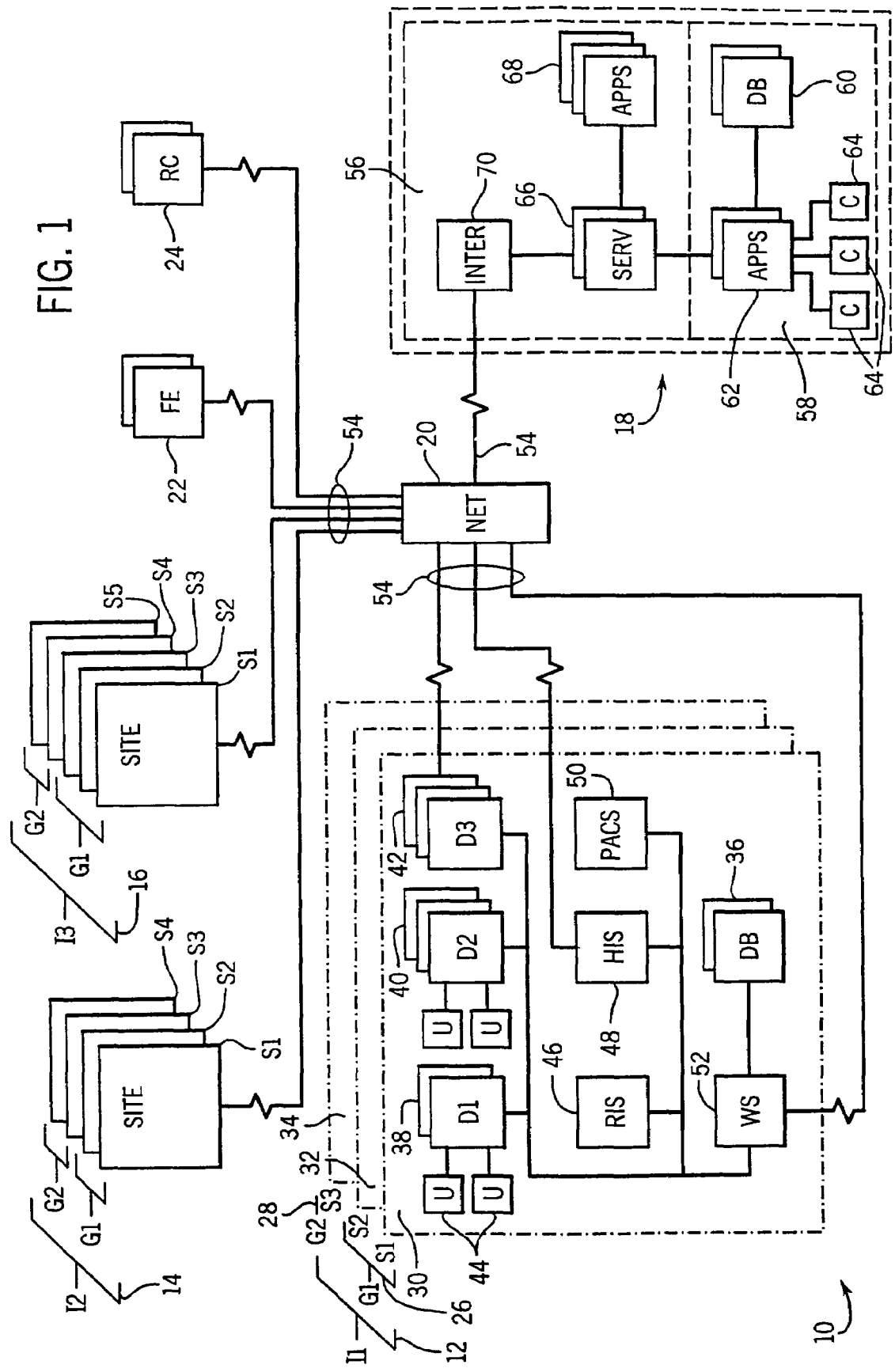
FIG. 1 is a diagrammatical representation of a service system for collecting and analyzing data in one or more medical institutions.

Turning up to the drawings, and referring first to FIG. 1, a service system 10 is represented for monitoring, data collection, data analysis, and reporting relating to biomedical equipment in one or more medical institutions. As illustrated, system 10 includes a plurality of institutions 12, 14 and 16, details of which are represented only for the first institution 12. In accordance with aspects of the present technique, any number of institutions may be serviced by a topography such as that illustrated in FIG. 1, or various modified topographies employing the techniques described below. System 10 further includes at least one service provider 18 which services the biomedical equipment of the institutions, collects and analyzes data on the equipment, and provides reports relating to the equipment inventory, performance, and so forth. In the illustrated embodiment, the institutions and the service provider may be linked via a network 20, such as the Internet. In a general implementation, the system may also permit access of data records by field engineers or technicians 22, and by remote clients 24. The field engineers and remote clients may, where appropriate, access or input data via mobile computer systems, remote computer terminals, and so forth.

Within each institution, a variety of functional portions or subdivisions may be defined, and data collected and analyzed in accordance with such functional portions. In the embodiment of FIG. 1, for example, institution 12 includes two functional groups 26 and 28, and three facility sites 30, 32 and 34. Sites 30 and 32 comprise group 26, while site 34 forms group 28. As will be described below, the present technique facilitates a collection and centralized storage of biomedical equipment data for individual sites, individual departments within the sites, institutions, and logical groupings. By way of example, where an institution includes sites in geographically dispersed locations, each site may be accounted for separately, but with the equipment data being referenced by site and institution, permitting an overview by either the site or the institution. Similarly, logical groupings, such as by political subdivisions (e.g., state, country, city) or fiscal or taxing jurisdictions may be specified and the data accordingly referenced.

Within each site, a variety of departments and systems may be designated and interfaced with one another. A centralized database 36 is compiled including data relating to biomedical equipment maintained (e.g., owned, managed, leased) by the institution. It should be noted that the database could be stored on any suitable memory device, and multiple memory devices, as shown, may be provided for storage of all or part of the database, or to provide backup and redundancy in storage. In general, however, the centralized database forms, for the user, a central repository for biomedical equipment data which can be accessed, processed, transferred, stored, and maintained to facilitate the tracking, management, planning, and other decision-making.

In the embodiment of FIG. 1, institution 12, at site 30, includes a variety of departments 38, 40 and 42. Depending upon the mission of the institution, these departments may include radiology departments, emergency care facilities, neonatal care facilities, oncology units, and so forth. Within each department, biomedical equipment will be maintained for providing medical care to in-patients and out-patients. In the present context, the biomedical equipment may include a wide range of disposable and non-disposable resources, such as patient monitors, input and readout devices, and so on. Generally, however, the biomedical equipment may also include elements of the physical plant of the institution, including beds, wheelchairs, computer systems, and so forth. In certain departments the equipment may further include imaging stations, scanners, probes, coil assemblies, and so forth. The equipment of each department is available for operation by nurses, clinicians, physicians, and other users, as indicated diagrammatically by reference numeral 44 in FIG. 1.

In addition to the biomedical equipment assigned to each department, the institution may include additional systems which are interfaced in the institution information system. For example, a radiology department information system (RIS) 46, a hospital information system (HIS) 48, a picture archiving and communication system (PACS) 50, and a similar information management systems may be provided. One or more management stations 52, such as a conventional computer workstation, is provided, preferably at each site, for reviewing reports and data generated as described below. It should be noted that a variety of such management stations may be provided, including fully or partially enabled management stations within each department. Various departments and systems within the institution will be provided with configurable network interfaces, such as modems or other network connections, so as to facilitate transmission and reception of data via network links 54 and network 20.

Service provider 18, which may function partially within the institution itself, includes processing capabilities for accessing, analyzing and reporting on data collected by the institutions on the biomedical equipment. It should be noted, however, that in the embodiment illustrated in FIG. 1, the service provider 18 may maintain facilities remote from one or more of the institutions and one or more of the facility sites, with data being transmitted between the institutions and the service providers via network 20. In the embodiment illustrated in FIG. 1, service provider 18 includes processing capabilities divided into a first processing space 56 and a second processing space 58. As described below, to maintain heightened security for data stored by the service provider, processing space 58 may be separated from space 56 to substantially limit access to processing space 58 from users outside the service provider system. In the present context, space 58 serves to store biomedical equipment records, to process data from the records, and exports data files for generation of reports within processing space 56. Thus, one or more databases 60 are maintained by the service provider 18, with processing capabilities in a form of specific applications 62 provided for storing, associating, analyzing, and extracting data from the database. Clients 64 may access the applications for performing the data manipulation functions at the service provider. One or more servers 66 are linked to the applications 62 to receive data files used as the basis for generating equipment reports. Additional applications 68 serve to format and process the reports. Finally, a network interface 70 is provided, such as including a router, modems, or similar network interface circuitry, for receiving data and transmitting data and reports to the medical institutions from the service provider.

Figure 2:
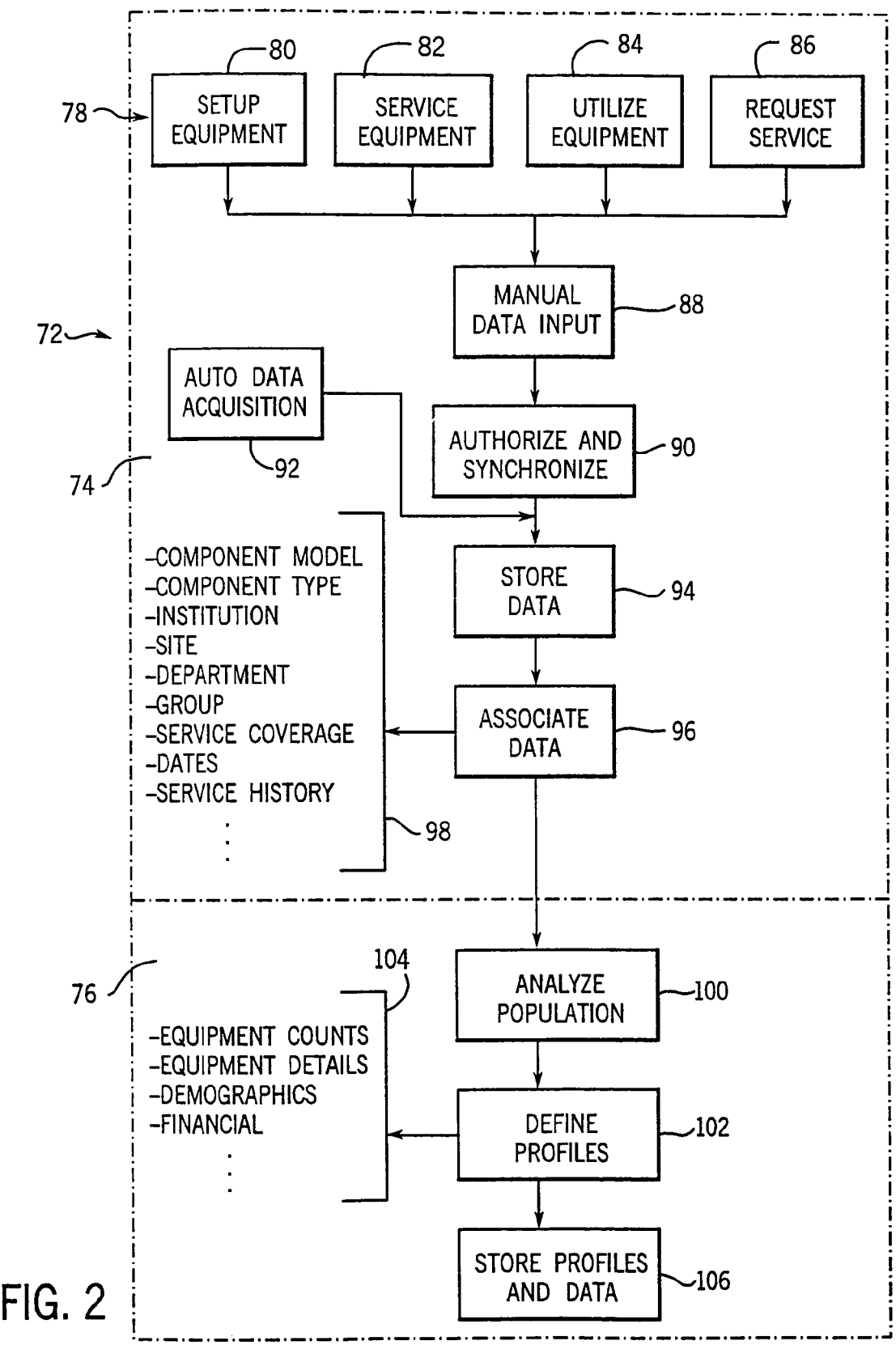
FIG. 2 is a flow chart representing exemplary control logic for collecting and analyzing the data system of the type illustrated in FIG. 1.

FIG. 2 represents exemplary logic for accessing or collecting, storing, and analyzing biomedical equipment data in a system of the type illustrated in FIG. 1. The processing illustrated in FIG. 2 may be logically subdivided into a data collection/storage/association sequence 74, and a population data analysis sequence 76. Within the sequence 74, data is collected for biomedical equipment within departments, sites, groups and institutions either manually, as indicated at reference numeral 78, or by automatic acquisition. Any suitable data input technique may be employed, typically including manual input via a workstation, laptop computer, handheld device, and so forth. Thus, as illustrated in FIG. 2, input may be by equipment setup upon its initialization, as indicated at reference numeral 80, or by subsequent servicing (i.e., as individual equipment components are serviced) as indicated at reference numeral 82. Other data may be manually input as the equipment components are utilized as indicated at 84, or upon specific service requests as indicated at reference numeral 86. At any one of these or other points in the operation of the biomedical equipment, the data relating to the equipment is thus manually input as indicated at reference numeral 88. To limit access to the data input system, and to maintain the integrity of the data, an authorization and synchronization sequence 90 is preferably implemented, such as through password protection, permitting authorized personnel only or authorized stations to input equipment data. Synchronization is performed to maintain up-to-date equipment data once the input is performed.

As an alternative to manual data input, certain automatic data acquisition may be performed as indicated at reference numeral 92 in FIG. 2. Automatic data acquisition may include polling of certain equipment, such as at regular intervals or according to a regular schedule. Networked equipment may thus be tracked and its performance monitored through data stored at the equipment and transmitted at step 92. Following either step 90 or 92, the data is stored as indicated at reference numeral 94. As noted above, the data may be stored at one or more storage devices, but with the data being associated in a centralized database for the institution. Again, the centralized database may be located physically at one or more of the institution sites, or off-site, such as at a location of the service provider 18.

At step 96, the data collected for the biomedical equipment is associated in the centralized database in accordance with any number of logical references. The data itself preferably includes references which facilitate or comprise the association as indicated at reference numeral 98. Thus, the component data may include both the identification of the component, the component model, including its manufacturer and model designation, and a component type, typically indicated by the function of the equipment. The data also preferably includes a reference representative of the institution, the site at which the components are located, the departments to which the components are assigned, if assigned, and the group designation for associating the departments or sites logically. The service data for each component also preferably includes a reference to service agreements or contracts for all or partial coverage of the components, including original warranty data and after-purchase service contracts or subscriptions. Relevant dates are preferably included, such as the date of purchase or entry into service, dates of servicing, and expiration or renewal dates for service arrangement coverage. Moreover, specific service history information may be included, where individual components have been regularly serviced or serviced on an as-needed basis. Such service history data may also include error codes, service request records input by the institution or users, breakdown records, downtime records, subcomponent replacement records, and so forth.

The population data analysis sequence 76 permits benchmarking or profiling of specific institutions and groups of institutions in accordance with equipment usage characteristics and other considerations. Where the service provider has access to equipment records for a range of institutions, the records are preferably analyzed to identify commonalities between the institutions, sites, departments, and groups. Such analysis may include consideration of the types of institutions, the types of departments, the types of equipment utilized, and the utilization characteristics (e.g., number of components, duty imposed on components, replacement or service records, and so forth). Based upon the analysis, characteristic profiles are identified which correspond to typical institutions, sites, departments, or groups that may be used as a basis for comparing a particular institution by equipment inventory and utilization for benchmarking purposes. It should be noted that benchmarking analysis preferably results in profiles which do not identify any individual institution, but which identify only a larger groups of institutions (such as groups of 20 or more) considered representative of a particular profile. The profiles, defined at step 102, may thus include reference data 104 such as equipment counts, equipment details, demographics, and financial profiles. At step 106 the profiles and corresponding reference data are stored, preferably in the database for the service provider, for future reference in benchmarking and service planning as described below.

Figure 3:
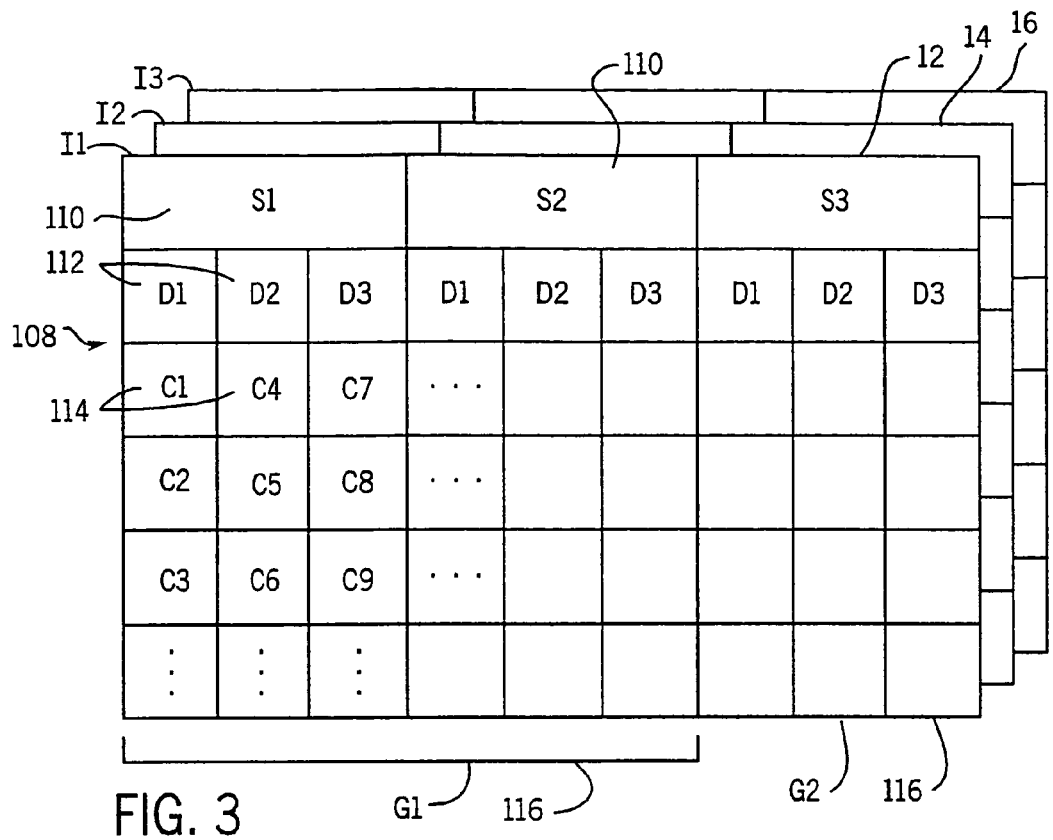
FIG. 3 is a diagrammatical representation of data records including data associated with institutions, sites, departments, groups, and components collected and processed in accordance with the aspects of present techniques.

The biomedical equipment records stored in the centralized database thus form a dataset or structure which permits and facilitates analysis by institution, site, department, group, component, component type, and other reference features. The database records may be considered to form a multi-dimensional data matrix structure which inter-relates these various aspects of the equipment component data as illustrated in FIG. 3. As shown in FIG. 3, the data record 108 for an institution 12 may thus include references 110 to specific facility sites at which equipment components are located. Additional departmental records 112 specify the department to which equipment components are assigned. Records for each department and site are then maintained for each component at reference numeral 114, including the identification and service information of the type described above. Moreover, the site, department, and component records may be associated by group designations 116. Where additional institutional records are available to the service provider, these may form a similar databases as illustrated in FIG. 3, permitting the analysis of groups of institutions to establish the profiles mentioned above.

Figure 4:
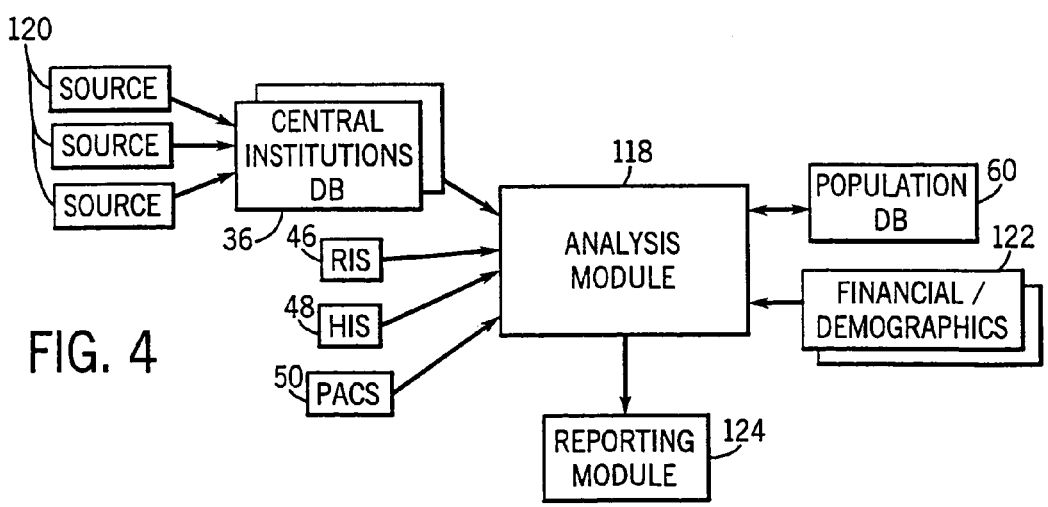
FIG. 4 is a data flow diagram illustrating the multiple sources of data utilized in analysis and reporting of institutional biomedical equipment data.

It should be noted that the present technique provides not only a centralized database for maintaining medical institution equipment records, but integrates a wide range of informational sources both at the institution and sources available to a service provider. FIG. 4 illustrates diagrammatically an example of the types of information sources which are integrated through the present technique. As described below, an analysis module 118 is provided either at the institution, or preferably at the service provider for accessing and analyzing the equipment records. The analysis module may incorporate a range of analysis algorithms, search techniques, and software applications, for deriving useful management data from the component records. In a general sense, the analysis module performs counts, statistical analysis, and associations of the equipment components by site, department, institution, group and manufacturer, as well as by any other references provided in the component records. The analysis module draws such information from the institutional database 36, as well as from other information systems of the institution, such as the RIS 46, the HIS 48, any PACS 50 present in the institution, or other institutional information systems. Again, the central institution database 36 may, in turn, obtain information from various sources, designated generally by reference numeral 120 in FIG. 4, such as departmental data entry systems, stationary or mobile data input devices, field engineer or service personnel laptops, and so forth. Similarly, analysis module 118 accesses information from population databases 60, such as for comparison in benchmarking, as well as financial, demographics, and other input 122, which may include publicly available sources, such as searchable databases, industry-specific databases, and so forth. Based upon analysis performed by the analysis module 118, a reporting module 124 is provided for generating and delivering reports representative the component records, and analysis derived from the component records.

Figure 5:
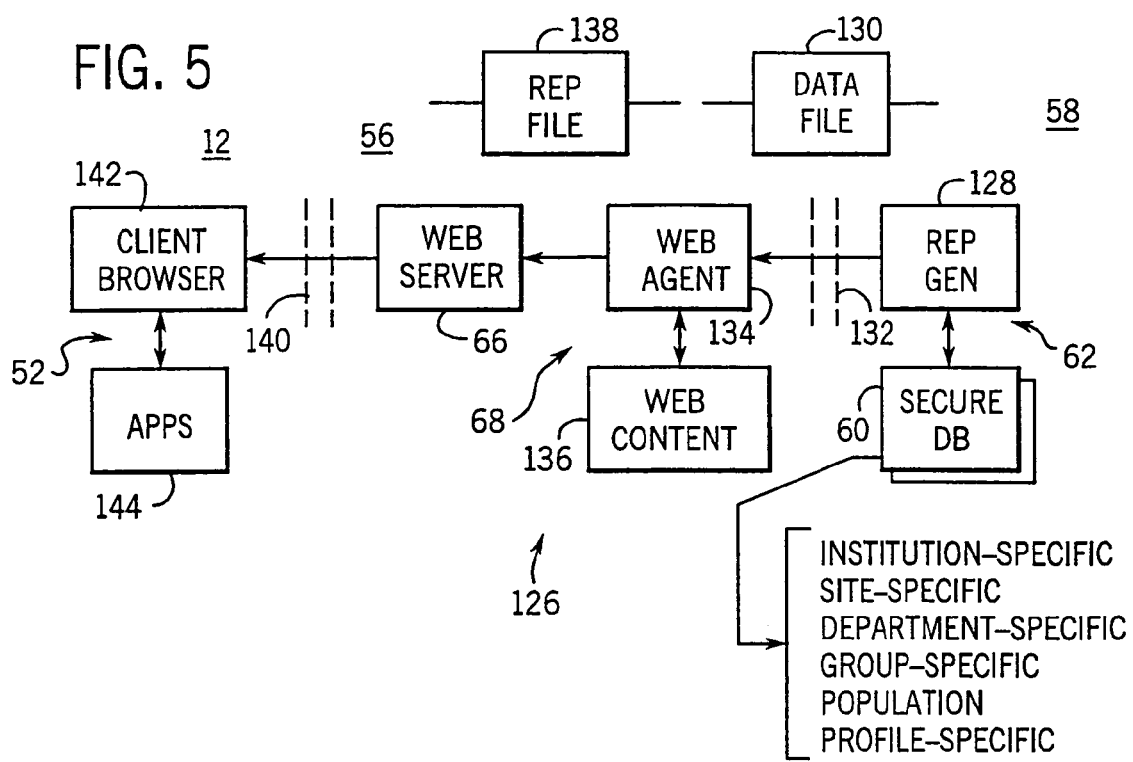
FIG. 5 is a work flow diagram illustrating functional components for securely generating reports based upon collected equipment data and for delivering the reports to a medical institution.

FIG. 5 is a diagrammatical representation of reporting workflow, designated generally by reference numeral 126, for operation of the analysis and reporting modules of FIG. 4. As shown in FIG. 5, the service provider secure database 60 is maintained in the secure processing space 58. Among the software applications 62 operative in the secure processing space 58, is a report generation application 128, which forms part of the reporting module represented generally at reference numeral 124 in FIG. 4. On a periodic basis, or upon request, the report generation application 128 accesses the data record 108 (see, e.g. FIG. 3) for the institution, and calculates or derives any inter-related data not already contained in the record for use in a management report or reports to be transmitted to the medical institution. In the example illustrated in FIG. 5, the data record includes information which institution-specific, site-specific, department-specific and group-specific. Moreover, database 60 may also include a data representative of known populations of medical institutions, sites, groups, or components, as well as pre-calculated data which is profile-specific. As noted above, the profiles generated based upon known population data may categorize institutions and other logical groupings by size, demographics, and so forth. Report generation application 128 produces a data file 130 containing data or fields of data, which is then exported via a firewall 132 to processing space 56.

Within processing space 56 additional hardware and software components are provided for translating the data file 130 into one or more report files. Thus, in the illustrated embodiment, applications 68 within the processing space 56 include a web agent 134 which is adapted to place data from file 130 into a predefined report template. Other web content, and input for generating the report is provided in one or more files 136. By integrating the data file and web content in the predefined report template, a report file 138 is generated, which may be adapted for presentation in any suitable manner, such as an HTML page on a conventional web browser. The report file 138 is then stored and is available for distribution via a web server 66.

In a present implementation, the web server 66 transmits the report file 138 via a configurable network link, such as the Internet, and through a firewall 140. At the medical institution 12, and typically at a management station 52, a client browser application 142 facilitates viewing and navigating through various portions of the report as described more fully below. Additional applications 144 may be available for manipulation of the report, formatting of the report, printing of hard copies and so forth.

Figure 6:
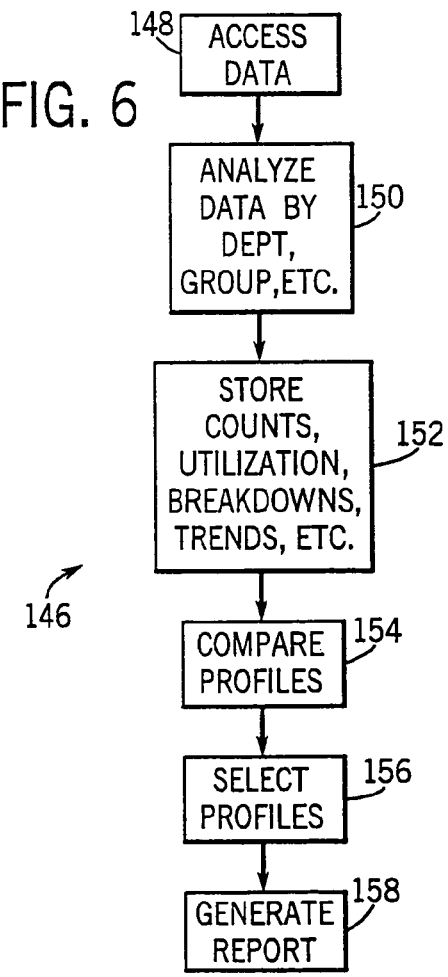
FIG. 6 is a flow chart illustrating exemplary control logic in departmental and group data processing in accordance with aspects of the present techniques.

As noted above, the present technique permits analysis of biomedical equipment data by various functional portions of a medical institution, such as by department or group. The data stored in the centralized database and accessed by the service provider is thus referenced by the functional portions, typically a department to which equipment components are assigned, or a site and group in which the components are located. FIG. 6 illustrates exemplary steps in control logic for processing the data to generate reports of equipment by department, group, site, or other logical division.

As shown in FIG. 6, at step 148, the data is accessed from the centralized database, and at step 150 the data is analyzed by the desired logical subdivision, such as the department or group. In a presently preferred embodiment, data is analyzed to identify the number of each component model and type, as well as to determine utilization parameters (e.g., time utilized or operations performed), breakdowns, error codes, trends, and so forth. Moreover, current data may be analyzed along with historical data stored in the centralized database, or in a historical database, to identify trends in these parameters over time. Thus, the analysis performed at step 150 may identify increases or decreases in the numbers of equipment components, increases or decreases in errors, breakdowns, and so forth. At step 152, the data generated by the analysis of step 150 is stored for later use in generating a report to the medical institution as described above. At step 154, all or some of the data originally collected, or derived from the original data, may be compared to reference data for similar institutions in accordance with predefined profiles as described above. The data itself may serve as the basis for selecting a comparable profile after the comparison of step 154, as indicated at step 156. Based upon the selected profile, benchmarking parameters may be generated which may provide an overview of the equipment inventory, performance, utilization, and servicing of the biomedical equipment of the institution with comparable institutions as defined by the profile. At step 158 a report is generated in accordance with the department, site, and group designation as described above with respect to FIG. 5.

Figure 7:
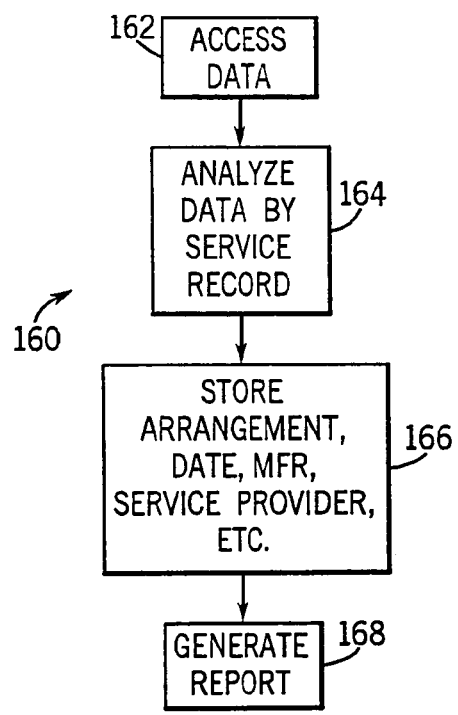
FIG. 7 is a flow chart illustrating exemplary control logic for service arrangement analysis and processing.

The present technique also permits detailed analysis of service arrangement coverage for biomedical equipment. As indicated by the control logic 160 summarized in FIG. 7, processing of the stored data to identify a service arrangement coverage begins at step 162 where the data is accessed. At step 164, the equipment records are analyzed by service record, to identify the equipment identification, its type, any existing warranties, service arrangement and subscriptions, and so forth. It should be noted that this information may include designations by department, site, group, or any other appropriate subdivision of the institution as summarized in FIG. 6. The resulting data summaries are stored at step 166 for generation of a report at step 168.

Figure 8:
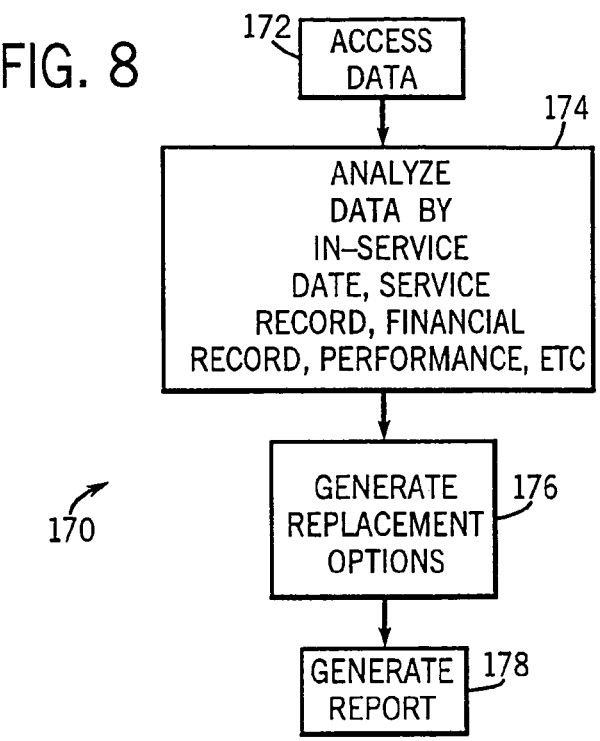
FIG. 8 is a flow chart illustrating exemplary control logic for equipment replacement and planning processing.

An additional functionality of the present technique permits the equipment data to be analyzed for scheduling or planning replacement of equipment, expansion in inventory, reductions in inventory, servicing, and so forth. Exemplary logic in the planning processing is summarized in FIG. 8 and designated generally by reference numeral 170. The processing 170 begins with access of the data at step 172, followed by analysis of the data by parameters such as the in-service date, the service record, financial records, performance records, and so forth. For example, specific biomedical equipment components may be scheduled for replacement a predetermined time after they are placed in service, such as in accordance with depreciation schedules, scheduled turnover of equipment, and so forth. Moreover, service records may provide a forecast of anticipated replacement needs for the equipment. Similarly, error codes or breakdown records may serve as the basis for forecasting possible replacement of the components. Where appropriate, anticipated changes in demographic information may also be used in the analysis of step 174, such as to plan for future expansions or reductions in inventory in accordance with anticipated needs of the institution. It should also be noted that, where desired, the replacement and planning processing of FIG. 8 may be performed for specific departments, sites, groups and other functional portions of the institution. At step 176, based upon the analysis of step 174, counts and types of equipment replacement are forecast and stored. Where desired, these forecasts may include accounting for anticipated costs of replacement, such as based upon current costs of the replacement items. At step 178 a planning report is generated based upon the analysis and replacement options.

Figure 9:
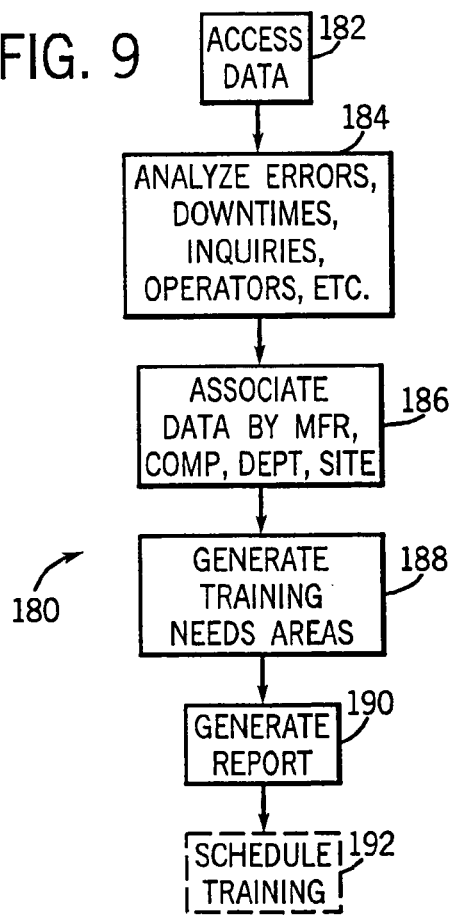
FIG. 9 is a flow chart illustrating exemplary control logic for analysis of data to determine possible areas for staff training.

A further type of processing which may be facilitated by the present technique is directed to identifying potential training needs based upon utilization of the biomedical equipment components. FIG. 9 represents steps in exemplary control logic for carrying out this processing, as indicated generally by reference numeral 180. The processing begins at step 182 where data for the components is accessed from the centralized database. At step 184, the data is analyzed to identify factors which may be indicative of a need for staff training. By way of example, such factors may include logged errors, downtimes, service or procedural inquiries, and so forth. In addition to identification of the particular components and training-indicative parameters, the data may also be analyzed to identify specific operators or users who may benefit from additional training. At step 186 the data is associated to identify the training needs by factors such as the equipment manufacturer, the component type, the department, the facility site, and so forth. Based upon the analysis made at steps 184 and 186, training needs are identified at step 188, and a report reflecting possible needs is generated at step 190. Again, the report generated at step 190, which may be generated in accordance with FIG. 5, may indicate specific training needs for specific equipment or equipment types, and may identify specific departments, sites, groups, or even specific users which may benefit from the training. As an optional step, actual training may be scheduled as indicated at step 192.

Figure 10:
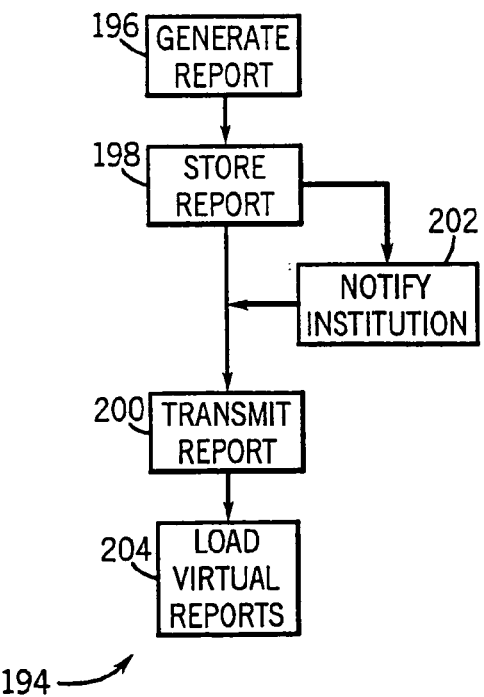
FIG. 10 is a flow chart illustrating exemplary control logic for report delivery based upon analysis summarizing the foregoing figures.

The various analyses and report generation steps described above, carried out generally in the secure manner summarized in FIG. 5, may produce reports which can be transmitted by various means to the management decision-makers of the medical institution. FIG. 10 illustrates a presently preferred manner of transmitting the reports via a configurable network. The process, designated generally by reference numeral 194, begins with generation of the report as indicated at reference numeral 196. At step 198 the report is stored, such as by generation of a data file, and combination of a data file with a report template to produce a report file or files. The report may be transmitted directly to the medical institution electronically, such as via a configurable network connection, as indicated at reference numeral 200. Alternatively, a notification may be sent to the institution, such as through the configurable network, notifying the institution that the report is available for downloading as indicated at step 202. The institution may then pull the report at any convenient time. Once the report is transmitted to the medical institution, it may be loaded and viewed on a management workstation as indicated at step 204. It should be noted, that the foregoing reports may be generated separately or in combination. Moreover, in a present embodiment, a single report file may include a wide range of "virtual reports" each of which includes details or user viewable pages with specific information relating to components, departments, sites, groups, and so forth.

The reports provided by the present technique may be formatted in any suitable manner. However, in a present embodiment, the reports are generated electronically, and are transmitted to the medical institution via a configurable network connection, such as in the form of HTML pages which can be opened and viewed in a conventional web browser or other display application. FIGS. 11-25 illustrate exemplary pages in such reports generated through logic such as that described above and based upon information collected in centralized database of a medical institution.

Figure 11:
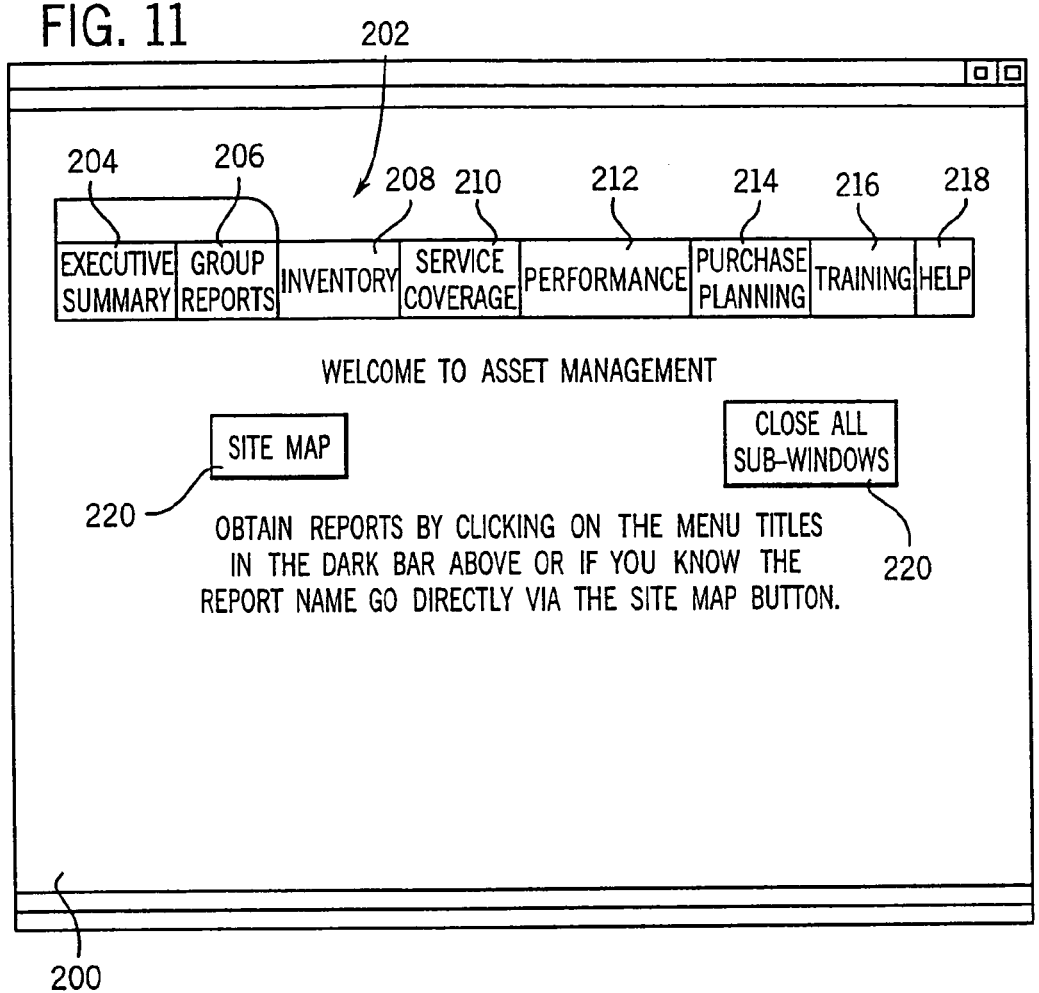
FIG. 11 is an exemplary graphical user interface screen, such as a browser screen, for accessing analyzed data and virtual reports.

FIG. 11 illustrates a summary or navigation page which is accessed in a conventional web browser for viewing additional report pages. As noted above, the report delivered in accordance with the foregoing techniques may include a wide range of data subdivided and associated in a manner so as to present information for individual equipment components, groups, sites, and so forth. In the present embodiment, the page illustrated in FIG. 11, designated generally by the reference numeral 200, provides for navigation through the various "virtual reports." The page preferably includes graphical user interface tabs or buttons 202 which can be selected by user for navigating through the more detailed reports. In the illustrated embodiment, such virtual buttons are provided for an executive summary 204, group reports 206, inventory analysis 208, service coverage analysis 210, performance analysis 212, planning analysis 214, and training analysis 216. Additional tools can be provided, such as a help tool 218, as well as alternative navigational tools 220, permitting the user to directly access virtual reports or to navigate or exit the report. As will be appreciated by those skilled in the art, various additional tools (not represented) can be provided, such as tools for reviewing previous pages, advancing to further pages, printing pages, searching through pages, and so forth.

Figure 12:
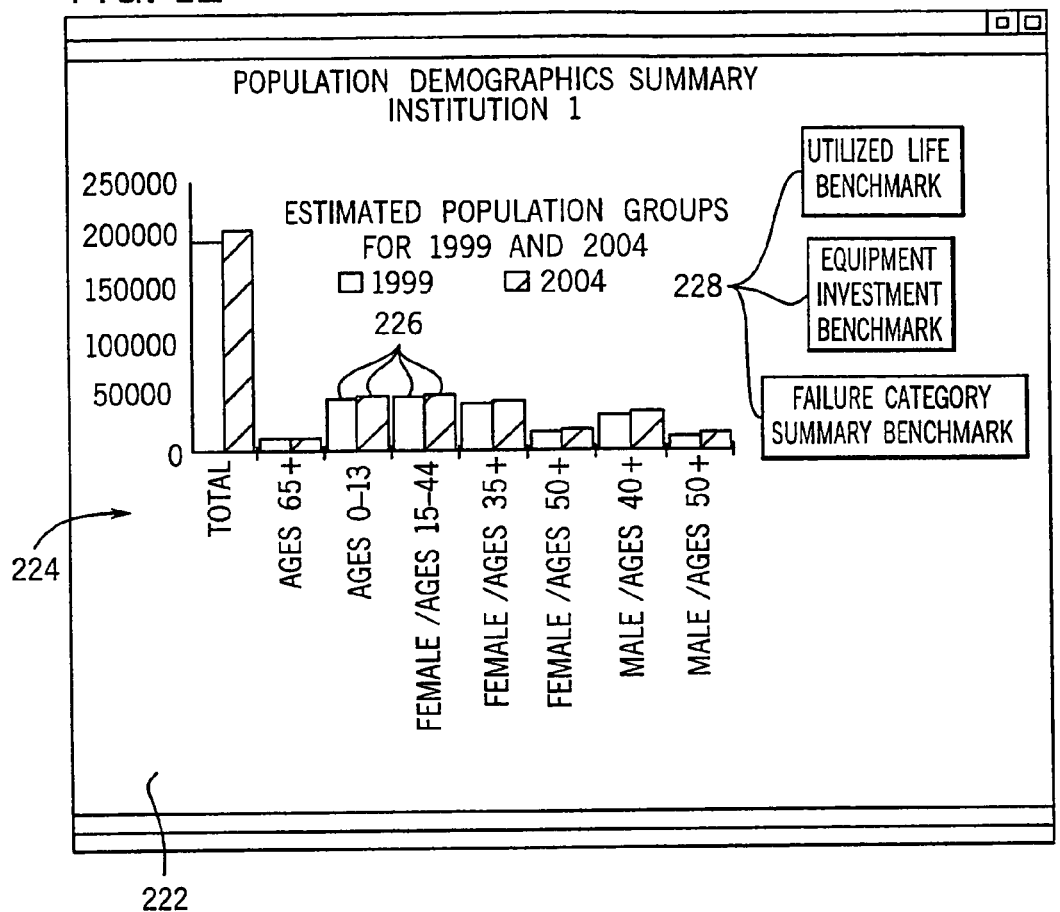

FIG. 12 illustrates an exemplary demographics summary page accessible through the executive summary tool 204 of FIG. 11. As noted above, the biomedical equipment data can be analyzed in accordance with demographic information for the institution so as to represent such factors as population groups within the institution (e.g., in-patients and out-patients), as well as the equipment utilized for patient care. In the summary page 222 of FIG. 12, a graphical summary display 224 provides an indication for the patient demographics of the subject institution. Also as noted above, where trending analysis is performed based upon current and historical collected data, trend graphics 226 may be provided. Also as noted above, where desired, equipment data collected for the institution, site, group, or department may be compared against profile data for known populations for similar institutions, and detailed benchmark reports comparing the subject institution to the selected profile may be accessed through virtual buttons 228. In the illustrated embodiment, such benchmarking is available through page 222 for comparing utilized life of equipment, investment, and failure records.

FIG. 13 illustrates a failure of benchmark summary table accessed through one of the virtual buttons 228 of FIG. 12. As illustrated in FIG. 13 the summary page 230 provides specific details for categories of equipment, as called out in a category column 232. When the collected equipment data is compared to similar data for a selected profile, the collected data may be classified in accordance with various classification ranges 234, to provide an indication of whether the subject institution's equipment performance falls within a statistical range of performance for the institution profile, or outside the range. Moreover, a summary may be provided as indicated at column 236 for equipment performance (e.g., failures) for equipment components covered by service arrangements. In the embodiment of FIG. 13, additional details are provided for the reference range in column 238 corresponding to ranges for the selected profile of the institution. Further comments and status data may be provided in additional column 240.

Figure 14:
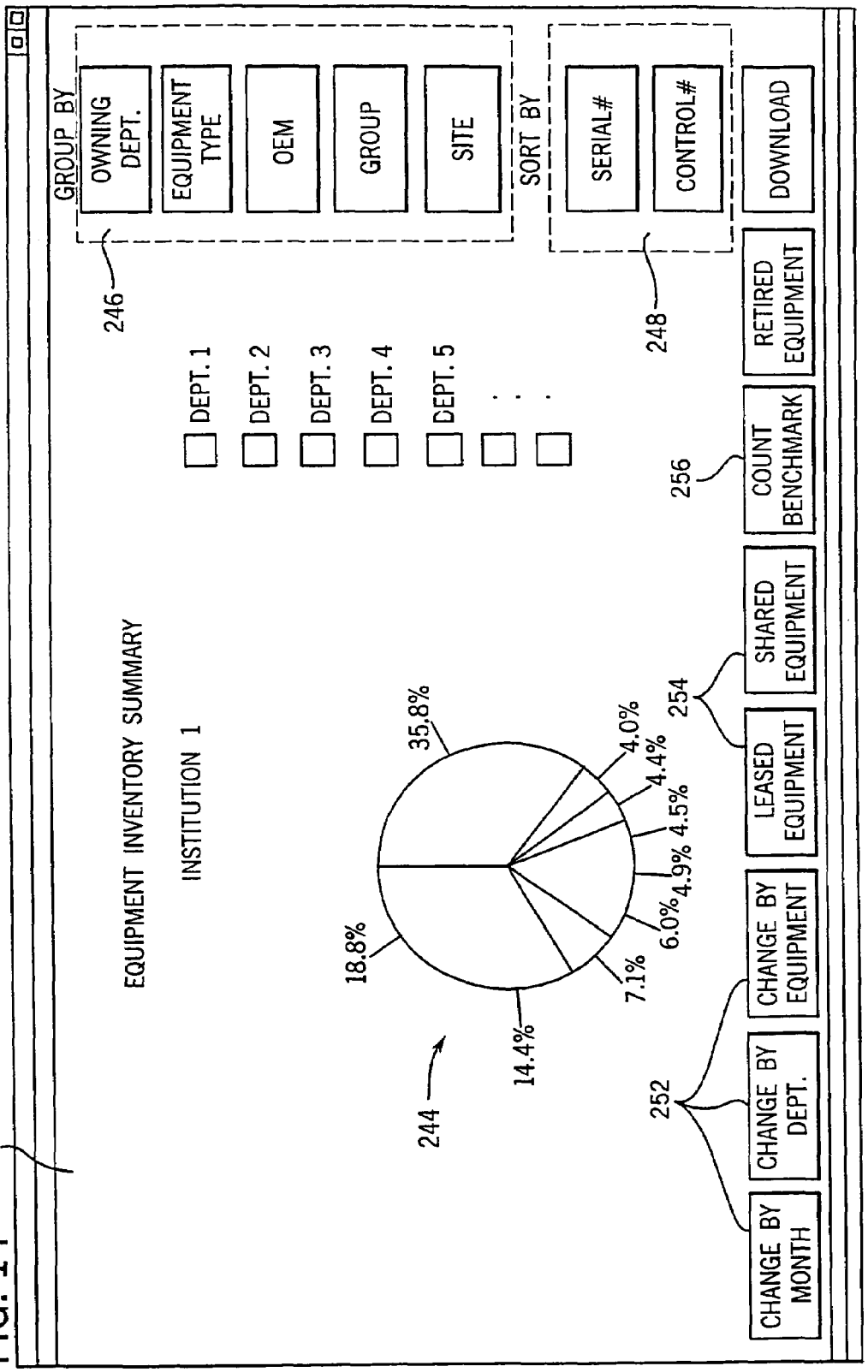

The biomedical equipment component data may also be summarized to analyze inventory on such bases as department, group, site, and so forth. FIG. 14 illustrates an inventory summary page by department as accessed through a virtual button 208 from the page illustrated in FIG. 11. As shown in FIG. 14, such inventory data may be summarized in a page 242, through the use of graphical techniques such as a graphical summary by department 244. The graphical techniques may present the data in any suitable fashion, such as through the pie chart illustrated in FIG. 14, through bar charts, line charts, or any other useful data presentation tools. In the embodiment illustrated in FIG. 14, the inventory summary page permits classification or sorting in accordance with a range of parameters stored for the equipment. By way of example, such classification may include the equipment type, the equipment manufacture, the group to which the institution or site locations belong, the site at which the equipment is located and so forth as indicated by the group tools 246. Additional sorting tools 248 may be provided, such as for viewing equipment details by serial number, control number, and so forth. As noted above, where equipment data is analyzed over a time range, such as by reference to historical equipment counts and performance, trending tools 252 may be provided, such as for viewing summary pages representing the changes by month, department, equipment, categories, and set forth. Moreover, depending upon the equipment title status, tools 254 may be provided for accessing pages presenting equipment inventory by title or ownership classifications. Finally, where benchmarking analysis is performed by reference to institution profiles and comparison to profiles for known institutions, benchmarking tools 256 may be provided for display of such comparisons.

Figure 15:
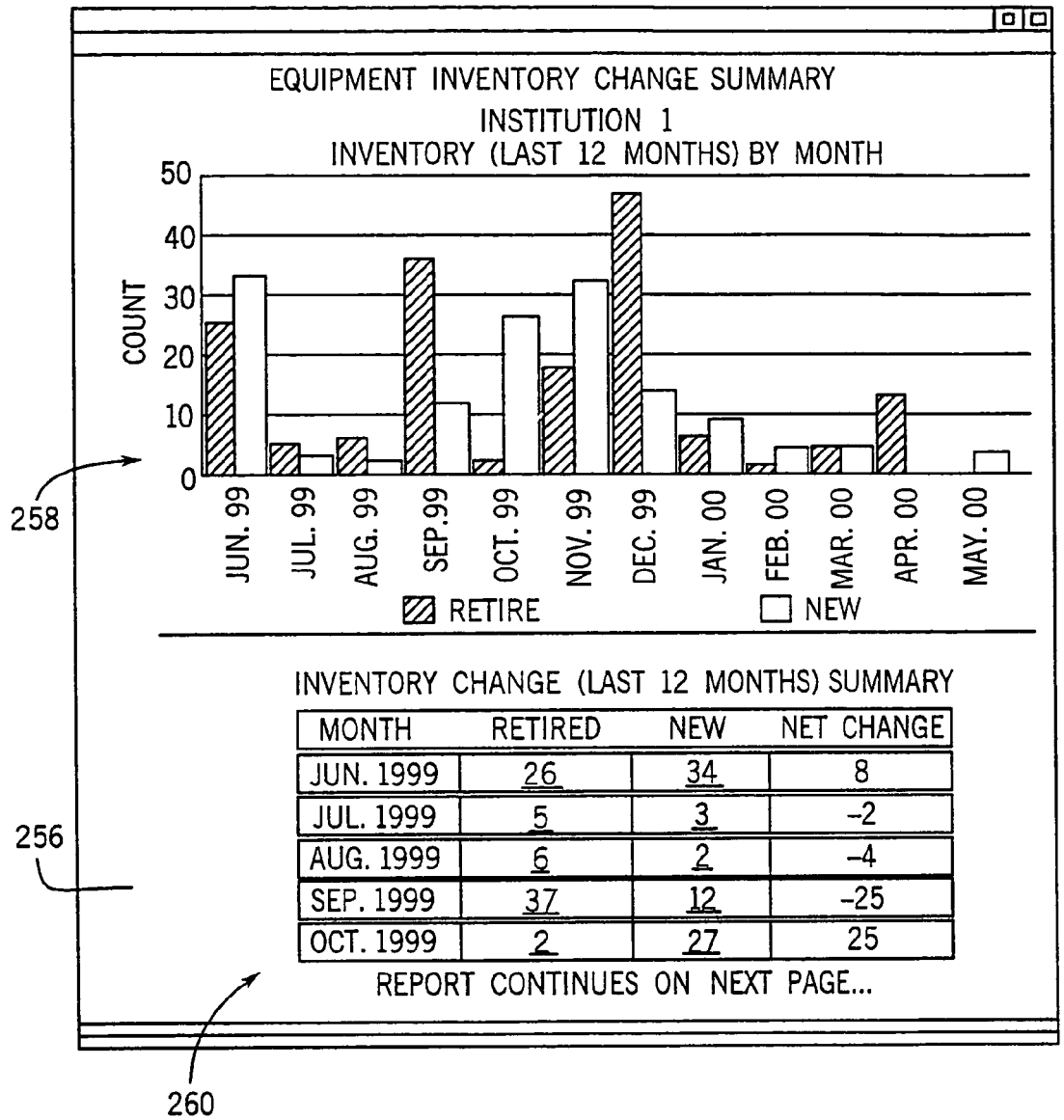
Figure 16:
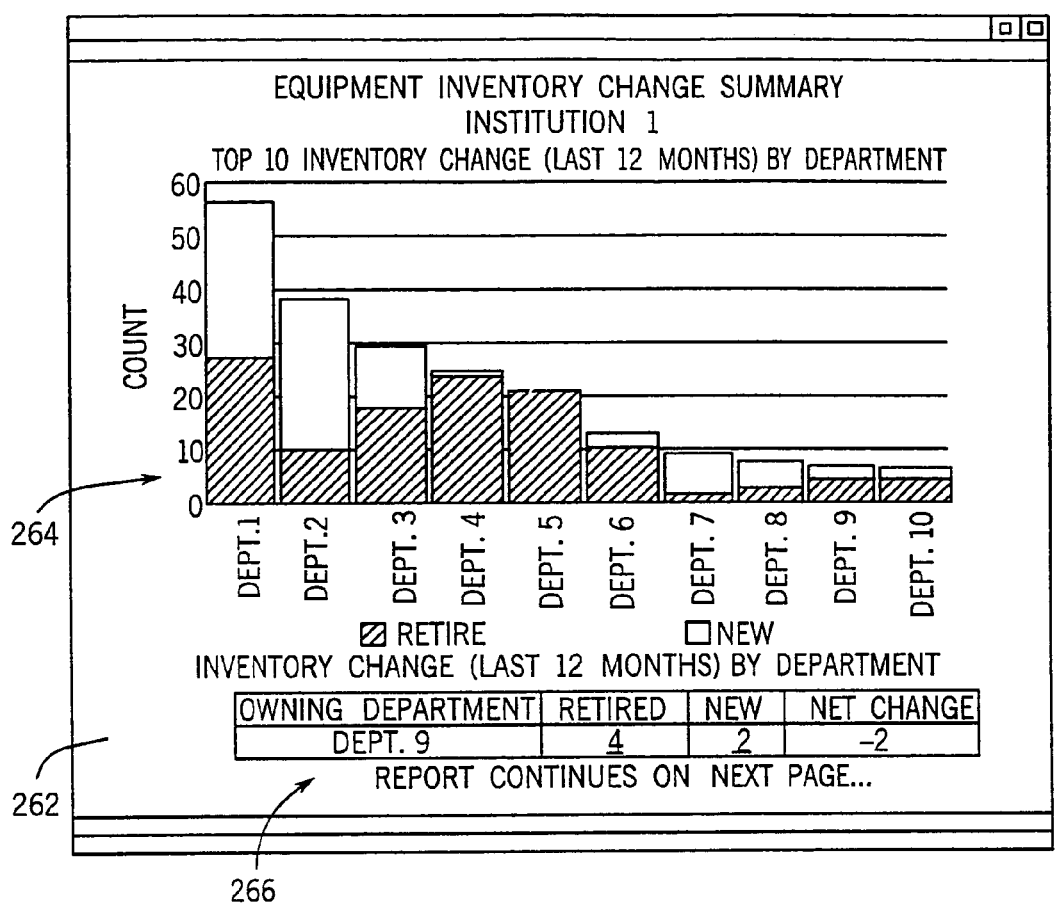

By way of example, FIG. 15 provides a page summarizing inventory trends or changes over a 12 months period, indicating both new equipment and retired equipment for an institution, as accessed via a virtual button 252 from FIG. 14. The inventory change summary page 256 provides a graphical summary 258 of the inventory changes. It should be noted that the graphical presentation may also present such changes by department, site, group, or any other desired functional portion of the institution. In the embodiment of FIG. 15, the information is also presented in a tabulated presentation indicating numerical counts for changes represented in the graphical presentation. Where desired, additional specific details may be offered through further pages, such as to provide an indication of the specific equipment or equipment types which have been retired or acquired. FIG. 16 illustrates an exemplary detailed summary page by department accessed through an additional virtual button 252 of FIG. 14. The departmental trend page 262 also provides a graphical indication 264 of the equipment changes per department, as well as a numerical count presentation 266 reflecting the changes.

As will be appreciated by those skilled in the art, the various presentations of inventory, inventory trends, inventory investment, and so forth, may be provided on various bases. For example, in the pages illustrated in FIGS. 14, 15 and 16, equipment counts are represented. However, by reference to the financial records for the institution or from a manufacturer, specific investment figures may be illustrated in a similar manner. Also, by reference to the financial records for individual components, and to regulations for taxing authorities (e.g., referenced by the group designations for the site locations) data presented in the reports may reflect book values for the equipment, depreciation to-date for the equipment, anticipated depreciation or book values, and so forth.

The comparison of the inventory data with similar data for institution profiles provides the opportunity to compare and benchmark the specific institution equipment performance. FIG. 17 illustrates an equipment count benchmark page accessed via a virtual tool 256 from the page of FIG. 14. When compared to the institution profile selected for the institution of interest, the benchmark information may compare such factors equipment counts, equipment investment, equipment performance, equipment failures, and so forth. Moreover, the information may be presented in accordance with various divisions or functional portions of the institution, such as departments, groups, sites, or as illustrated in FIG. 17 by sub-modalities. In the embodiment of FIG. 17, the benchmark presentation page 268 includes a category 270 for the equipment sub-modality, as well as a range classification column 272 indicating whether the basis for the comparison was within or outside a statistical range for the profile. An actual count column 274 is provided for each sub-modality, as well as a reference range column 276 for the specific profile selected. Other information, such as comments or status may be provided in a column 278. By way of example, in a present embodiment, where the profile population is insufficient to provide a reliable statistical basis for comparison (e.g., less than 20 institutions) a comment may be provided in column 278 indicating that this is the reason for a "no status" reference in the benchmark presentation.

Figure 18:
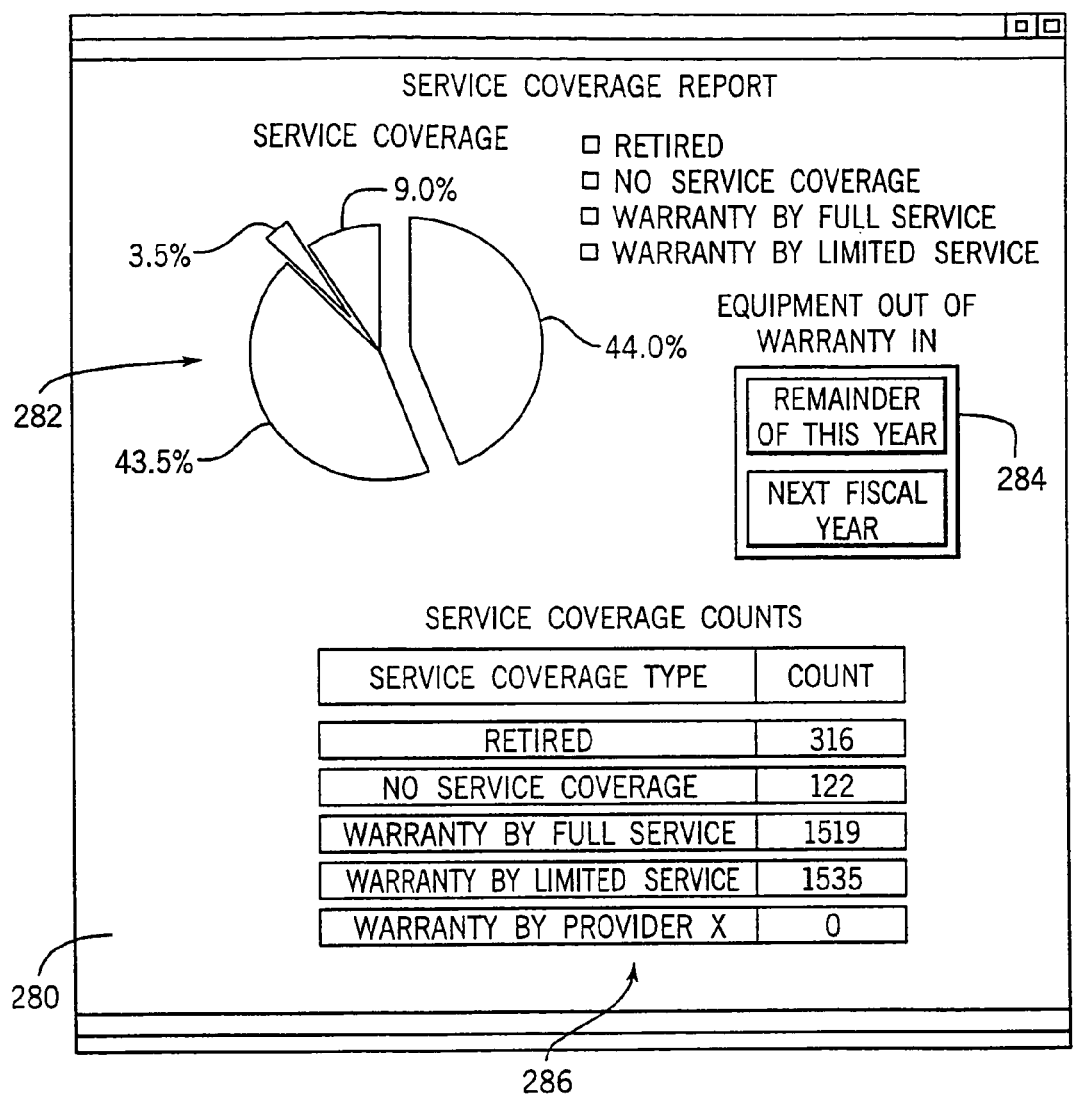

As described above, the present technique also provides an extremely useful tool for analyzing service coverage of biomedical equipment of the institution. FIG. 18 illustrates an exemplary report page summarizing service coverage for such equipment. The summary page 280 conveniently provides a graphical summary 282 for the level of service arrangement coverage or specific biomedical equipment. The page also provides tools 284 permitting the user to navigate to more detailed pages summarizing trends in service coverage, particularly service arrangements which will extend through a desired period and summaries of time periods during which service coverage will expire. Additional data presentations 286 may be provided for summarizing counts or quantities of various types of equipment which are covered by service arrangements.

FIG. 19 illustrates an exemplary detailed report of service arrangement coverage for biomedical equipment accessible from the summary page illustrated in FIG. 18. In the example FIG. 19, detailed information is provided in a summary page 288, and may be sorted in a variety of manners depending upon the analysis desired by the user. By way of example, designations or references may be provided by departments 290 to which the equipment is assigned, by site location 292 at which the equipment is located, or by group 294 to which the site belongs. The information may also be presented by equipment type 296, and equipment manufacturer 298. Where desired, more detailed reports for each of these classifications may accessible from the summary page. Additional details 298 may be provided, such as manual numbers, model numbers, and so forth. Where desired, acquisition dates for the equipment may be provided in column 300, particularly where such dates serve as the basis for warranty or other service coverage. Detailed identification numbers may be provided as indicated at reference numeral 302, specifically identifying pieces of equipment and reference codes used by the institution for designating the equipment. Moreover, where desired, specific identifications of service providers 304 and expiration and renewal dates 306 for service arrangements with the providers may be summarized. Such summaries thus provide decisionsmakers for the institution with powerful tools for grouping and analyzing service coverage arrangements for specific equipment, and for anticipating needed changes or renewals in such coverage.

Figure 20:
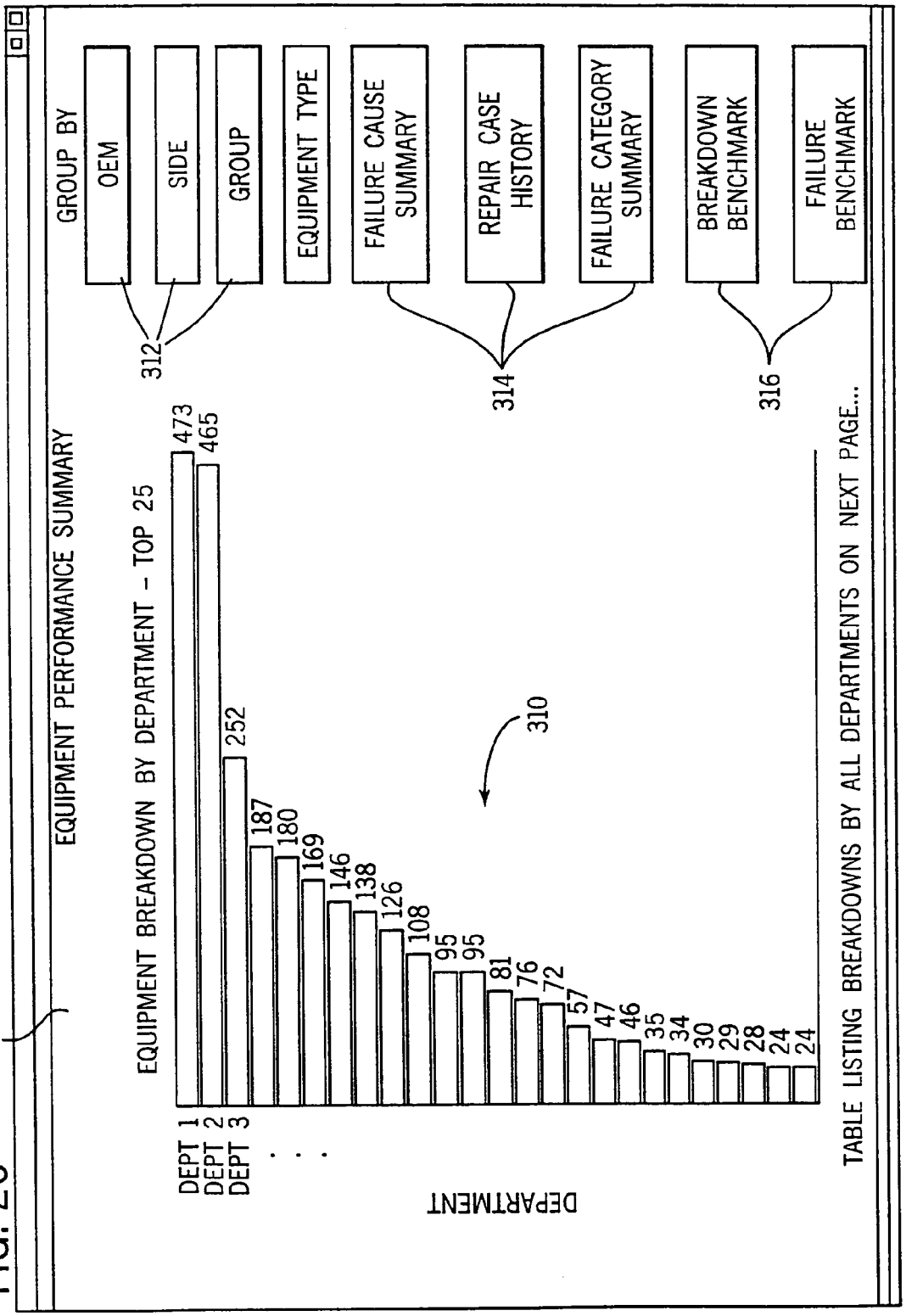

The equipment data stored in the centralized database for the institution may also be analyzed to identify parameters indicative of equipment performance. Such factors may include equipment utilization (e.g., number of days or cases for which the equipment was used) error codes, downtime, number of breakdowns, and so forth. An exemplary performance summary page 308 is illustrated in FIG. 20, accessible via a virtual button 212 from the main page of FIG. 11. In the exemplary embodiment of FIG. 20, the summary page provides a graphical summary 310 of specific equipment breakdowns by department. Similar presentations are available for other group designations, such as by equipment manufacturer, equipment site, site groups, and so forth, as indicated by the graphical buttons 312 in FIG. 20. Specific detailed analysis tools 314 may also be provided, such as for accessing virtual report pages summarizing causes of failure, repair histories, failure categories, and so forth. As noted above, the performance data may be compared against similar data for profiles of institutions derived from known populations of institutions, and benchmark pages may be presented through navigation tools 316, such as to provide breakdown benchmarking, failure benchmarking, and so forth.

Figure 22:
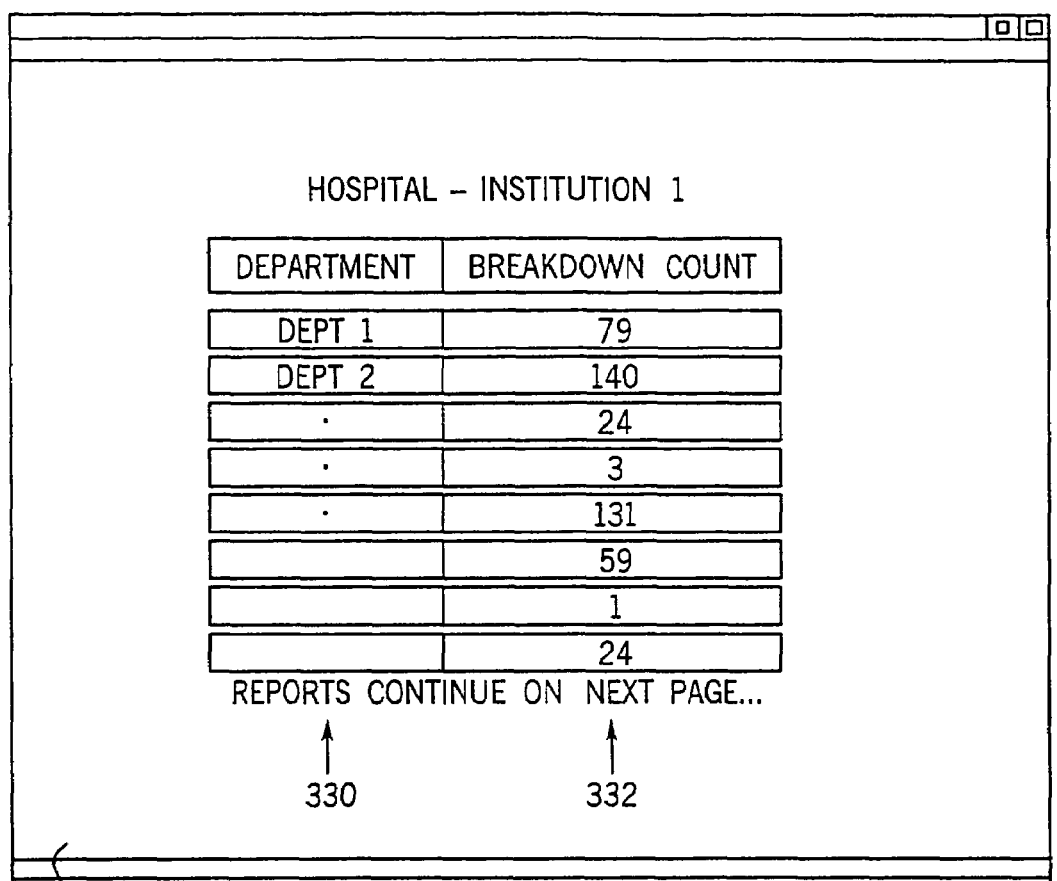

By way of example, FIG. 21 illustrates a summary page for equipment performance (referenced by breakdowns) for a specific department of an institution. The departmental summary page 318, in the illustrated embodiment, provides references to the manufacturer of the equipment, as well as the equipment designation as indicated by reference numeral 320. Breakdown summary information 322 is provided, including a count of the breakdowns and a summary of the performance over a desired analysis, such as a year. Specific identifications for the equipment are provided in columns 324, allowing for tracking of individual problematic equipment components, useful in analysis, replacement, and similar planning. Finally, additional details, such as time-in-service, and statistical information such as mean-time-to-repair, and mean-time-between-failures may be summarized as indicated at reference numeral 326. Further details may be accessible through detailed pages such as illustrated in FIG. 22. The detailed page 328 of FIG. 22 may present the performance information by functional portion of the institution, such as departments as illustrated at reference numeral 330, along with detailed analysis, such as a breakdown count as indicated at reference numeral 332.

Figure 23:
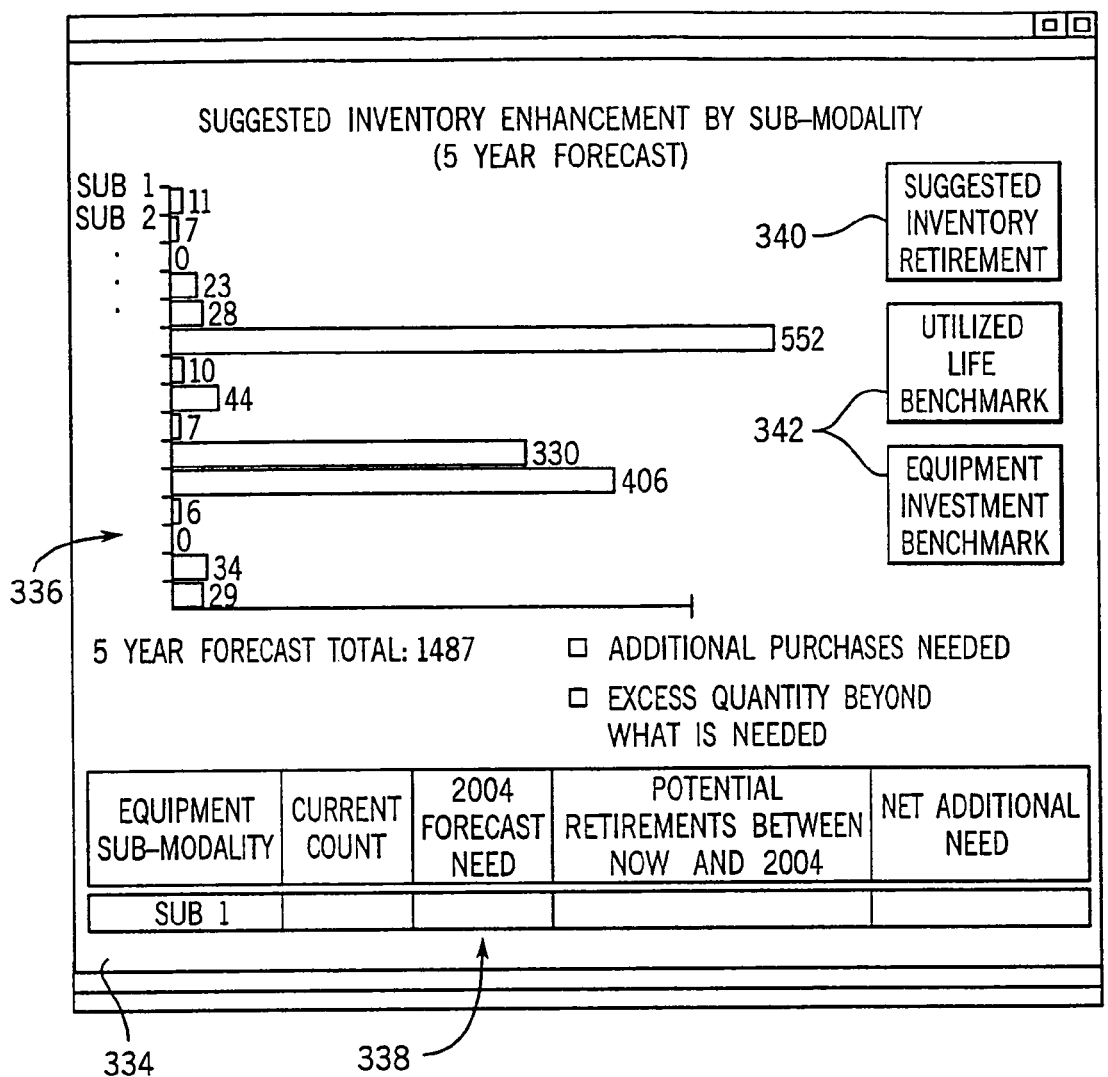

To aid in equipment management, forecasting, financial planning, and so forth, the present technique offers for data collection and reporting by analysis of potential needs for the institution, both in terms of newly acquired equipment, or retired equipment. Such forecasting tools may be based upon analysis of the equipment data stored in the centralized database, and upon factors such as the date at which the equipment entered into service, the anticipated life of the equipment, the depreciation period for the equipment, increases in anticipated demographics for the institution, and so forth. An exemplary forecast planning page 334 is illustrated in FIG. 23, accessed through a virtual button 214 from the main page at FIG. 11. As illustrated in FIG. 23, such pages may present forecasts by functional portion of the institution in graphical form 336. Such presentations may, as before, be subdivided by any suitable functional portion of the institution, such as departments, sites, groups, or as illustrated in FIG. 23, by sub-modality. The summary page may allow for additional navigation to suggested inventory changes, as indicated at reference numeral 340, as well as to benchmarking summaries for suggested equipment changes as indicated at reference numeral 342, providing comparisons of the suggested changes in the equipment inventory as compared to other institutions of similar profiles. Tabulated summaries of the data provided in the page may be summarized as indicated at reference numeral 338.

Additional, more detailed summaries accessible through the page illustrated in FIG. 23 are shown in FIGS. 24 and 25. As illustrated in these figures, a detailed planning page 344 may summarize specific changes suggested for the biomedical equipment, such as broken down by functional portion 346, in this case sub-modality. Current equipment counts (or equipment values) may be provided as indicated at reference numeral 348, as well as summaries of additions to, retirements from, and net changes in the inventory, as summarized at reference numeral 350. Even more detailed pages may be provided as shown in FIG. 25, such as through a long-term detailed forecast 352. A graphical summary 354 may be provided for the forecast, and a forecast may be subdivided by any suitable functional portion of the institution, sub-modality in the example of FIG. 25.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A method for generating reports for management of a medical facility, the method comprising the steps of:
   (a) storing data representative of operation of a medical facility in a data repository operative in a first processing space;
   (b) accessing data from the repository to populate a report;
   (c) transmitting the accessed data to a second processing space separated from the first processing space by a security device; and
   (d) generating the report in the second processing space based upon the transmitted data and a predefined report template.

2. The method of claim 1, wherein the data is accessed in accordance with a predetermined reporting schedule.

3. The method of claim 1, wherein the data is accessed in response to an operator prompt for report generation.

4. The method of claim 1, comprising the further step of generating a report template identifying data to be accessed in the first processing space, and wherein step (b) includes accessing data identified in the report template.

5. The method of claim 1, wherein the security device includes a firewall.

6. The method of claim 1, wherein the accessed data is stored in a data file and step (c) includes exporting the data file to a storage medium in the second processing space.

7. The method of claim 1, comprising the further step of automatically generating a notification message indicative of availability of the report generated in step (d).

8. The method of claim 7, wherein the message is transmitted to a user, and the report is maintained in the second processing space at least until the user accesses the report to a remote location.

9. The method of claim 1, wherein the second processing space is accessible via a wide area network.

10. The method of claim 9, wherein the second processing space is accessible via the Internet.

11. The method of claim 1, wherein the report is generated for a subscribing medical facility, and wherein the first processing space is inaccessible to the subscribing facility.

12. A method for securely generating reports of activities of a medical diagnostic facility, the method comprising the steps of:
   (a) storing data representative of activities of the medical diagnostic facility in a secure database operative in a first processing space;
   (b) defining a report template, the report template identifying data for presentation in a report;
   (c) populating a data file in the first processing space with data from the database as identified by the report template;
   (d) exporting the data file to a second processing space separated from the first processing space by a security device; and
   (e) generating the report in the second processing space based upon the template and the data file.

13. The method of claim 12, wherein step (a) includes storing data accessed from the medical diagnostic facility during automated data collection.

14. The method of claim 12, wherein the first processing space is inaccessible by the medical diagnostic facility.

15. The method of claim 12, wherein the second processing space is accessible by the medical diagnostic facility.

16. The method of claim 15, wherein the second processing space is accessible via a wide area network.

17. The method of claim 12, wherein the data file is populated in accordance with a predetermined report generation schedule.

18. The method of claim 12, wherein the report is stored in the second processing space until accessed by the medical diagnostic facility.

19. A method for securely providing reports relating to activities of a medical diagnostic facility, the method comprising the steps of:
   (a) storing data representative of activities of the medical diagnostic facility in a secure data repository operative in a first processing space;
   (b) generating a report data file in the first processing space in accordance with a predefined report template;
   (c) exporting the report data file from the first processing space to a second processing space securely separated from the first processing space, the second processing space being accessible by the medical diagnostic facility via a wide area network; and
   (d) generating a report based upon the template and the report data file.

20. The method of claim 19, comprising the further step of transmitting the report to the medical diagnostic facility via a wide area network.

21. The method of claim 20, wherein the wide area network includes the Internet.

22. The method of claim 19, wherein the data stored in step (a) is collected at least partially during automated data collection sessions between the medical diagnostic facility and a remote service provider.

23. A system for generating reports relating to activities of a medical diagnostic facility, the system comprising:
   a secure data repository operative in a first processing space for storing data representative of activities of the medical diagnostic facility;
   a report template identifying desired data for populating a report;
   a data access program module, operative in the first processing space for extracting the desired data from the repository;
   a second data repository operative in a second processing space securely separated from the first processing space for storing the desired data extracted by the data access program module; and
   a report generation program module, operative in the second processing space for generating a report based upon the desired data the report template.

24. The system of claim 23, wherein the data access program is configured to extract the desired data in accordance with a predetermined schedule.

25. The system of claim 23, wherein the second data repository is configured to store the report.

26. The system of claim 23, wherein the second data repository is accessible by the medical diagnostic facility.

27. The system of claim 26, comprising a server coupled to the second data repository for transmitting the report to the medical diagnostic facility.

28. The system of claim 27, wherein the server is configured to be coupled to a wide area network, and to transmit the report to the medical diagnostic facility via the wide area network.

29. A system for generating reports for management of a medical facility, the system comprising:
  means for storing data representative of operation of a medical facility, the means for storing operative in a first processing space;
  means for accessing data from the means for storing to populate a report;
  means for transmitting the accessed data to a second processing space securely separated from the first processing space; and
  means for generating the report in the second processing space based upon the transmitted data and a predefined report template.

30. The system of claim 29, further comprising means for notifying the medical facility of availability of the report.

31. The system of claim 29, further comprising means for transmitting the report to the medical facility.

32. The system of claim 31, wherein the means for transmitting the report includes a wide area network.

33. The system of claim 29, wherein the first processing space is inaccessible by the medical facility and the second processing space is accessible by the medical facility.

34. A computer program for generating reports for management of a medical facility comprising:
  at least one computer readable medium; and
  computer code stored on the at least one computer readable medium for carrying out the steps of storing data representative of operation of a medical facility in a data repository operative in a first processing space; accessing data from the repository to populate a report; transmitting the accessed data to a second processing space separated from the first processing space by a security device; and generating the report in the second processing space based upon the transmitted data and a predefined report template.

35. A computer program for securely generating reports of activities of a medical diagnostic facility comprising:
  at least one computer readable medium; and
  computer code stored on the at least one computer readable medium for carrying out the steps of storing data representative of activities of the medical diagnostic facility in a secure database operative in a first processing space; defining a report template, the report template identifying data for presentation in a report; populating a data file in the first processing space with data from the database as identified by the report template; exporting the data file to a second processing space securely separated from the first processing space;
  and generating the report in the second processing space based upon the template and the data file.

36. A computer program for securely generating reports of activities of a medical diagnostic facility comprising:
  at least one computer readable medium; and
  computer code stored on the at least one computer readable medium for carrying out the steps of storing data representative of activities of the medical diagnostic facility in a secure data repository operative in a first processing space; generating a report data file in the first processing space in accordance with a predefined report template; exporting the report data file from the first processing space to a second processing space securely separated from the first processing space, the second processing space being accessible by the medical diagnostic facility via a wide area network; and generating a report based upon the template and the report data file.

* * * * *